United States Patent [19]

Förster et al.

[11] Patent Number: 4,465,504

[45] Date of Patent: Aug. 14, 1984

[54] HERBICIDALLY ACTIVE NOVEL N-(2,2,2-TRIFLUOROETHYL)-N-ALKYL-AZOLYLOXYACETIC ACID AMIDES AND INTERMEDIATES THEREFOR

[75] Inventors: Heinz Förster; Volker Mues, both of Wuppertal; Bernd Baasner, Leverkusen; Hermann Hagemann, Leverkusen; Ludwig Eue, Leverkusen; Robert Schmidt, Bergisch-Gladbach, all of Fed. Rep. of Germany

[73] Assignee: Bayer Aktiengesellschaft, Leverkusen, Fed. Rep. of Germany

[21] Appl. No.: 350,520

[22] Filed: Feb. 19, 1982

[30] Foreign Application Priority Data

Mar. 13, 1981 [DE] Fed. Rep. of Germany ....... 3109582

[51] Int. Cl.$^3$ .................. C07D 277/34; A01N 43/76; A01N 43/78; A01N 43/82

[52] U.S. Cl. ............................................ 71/88; 71/90; 71/92; 548/129; 548/130; 548/132; 548/136; 548/138; 548/139; 548/144; 548/161; 548/163; 548/170; 548/183; 548/184; 548/185; 548/187; 548/188; 548/221; 548/226; 548/227; 548/229; 548/230

[58] Field of Search ............... 544/183, 184, 185, 187, 544/188, 129, 130, 132, 136, 138, 139, 144, 161, 163, 170, 226, 227, 229, 230, 221; 71/90, 92, 88

[56] References Cited

FOREIGN PATENT DOCUMENTS

| 4187 | 9/1979 | European Pat. Off. ................ 71/88 |
| 5501 | 11/1979 | European Pat. Off. ................ 71/88 |
| 18497 | 11/1980 | European Pat. Off. ................ 71/88 |
| 29171 | 5/1981 | European Pat. Off. ................ 71/88 |
| 37525 | 10/1981 | European Pat. Off. ................ 71/88 |
| 37938 | 10/1981 | European Pat. Off. ................ 71/88 |
| 44497 | 1/1982 | European Pat. Off. ................ 71/88 |

Primary Examiner—Robert Gerstl
Attorney, Agent, or Firm—Sprung, Horn, Kramer & Woods

[57] ABSTRACT

An N-(2,2,2-trifluoroethyl)-N-alkyl-azolyloxyacetic acid amides of the formula

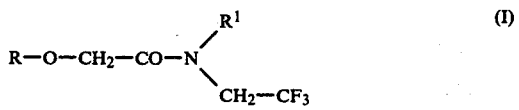

in which R and $R^1$ have the meaning given in the description, a process for the production of which is described, find use as herbicides. The intermediate products of the general formulae

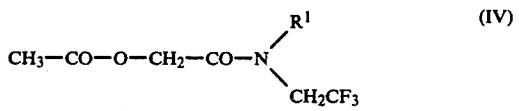

and

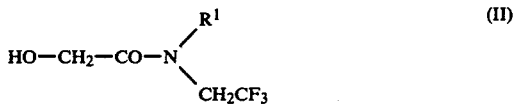

in which $R^1$ in each case has the same meaning as in formula (I), for the preparation of the compounds (I) are also new.

10 Claims, No Drawings

HERBICIDALLY ACTIVE NOVEL N-(2,2,2-TRIFLUOROETHYL)-N-ALKYL-AZOLYLOXYACETIC ACID AMIDES AND INTERMEDIATES THEREFOR

The invention relates to certain new N-(2,2,2-trifluoroethyl)-N-alkyl-azolyloxyacetic acid amides, to a process for their production and their use as herbicides, and to certain new α-substituted N-(2,2,2-trifluoroethyl)-N-alkyl-acetic acid amides as intermediate products for their production.

It has already been disclosed that certain substituted carboxylic acid amides, such as benzoxazol-2-yl-oxyacetic acid 1,2,3,4-tetrahydroisoquinolide, benzoxazol-2-yl-oxyacetic acid isobutylamide and 3-isopropyl-1,2,4-thiadiazol-5-yl-oxyacetic acid N-ethyl-N-butyl-amide, have herbicidal properties (compare European Published patent applications Nos. 5,501 and 18,497).

However, the herbicidal properties of these compounds are not always satisfactory from the point of view of the level of action and selectivity.

The present invention now provides, as new compounds, the N-(2,2,2-trifluoroethyl)-N-alkyl-azolyloxyacetic acid amides of the general formula

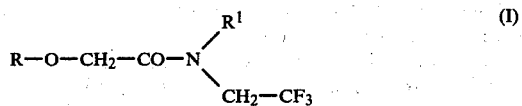
(I)

in which R represents a five-membered heterocyclic radical which contains an oxygen or sulphur atom and additionally contains 1 to 3 nitrogen atoms, and which is optionally substituted by halogen, cyano nitro, amino, alkylamino, arylamino, dialkylamino, alkylcarbonylamino, alkylcarbonyl, carboxyl, alkoxycarbonyl, carbamoyl, alkylaminocarbonyl, dialkylaminocarbonyl, arylaminocarbonyl which is optionally substituted by halogen, nitro or alkyl, aryl which is optionally substituted by halogen, cyano, nitro, alkyl or alkoxy; by an optionally halogen-substituted radical selected from aralkyl, alkoxy, alkenoxy, alkinoxy, alkoxycarbonylalkoxy, aralkoxy, aryloxy, alkylthio, alkenylthio, alkinylthio, alkoxycarbonylalkylthio, aralkylthio, arylthio, alkylsulphinyl, alkylsulphonyl, alkyl, alkenyl, alkinyl, alkoxyalkyl, aralkoxyalkyl, aryloxyalkyl, alkylthioalkyl, alkylsulphinylalkyl, alkylsulphonylalkyl, arylthioalkyl, arylsulphinylalkyl, arylsulphonylalkyl, carboxyalkyl and alkoxycarbonylalkyl; or by optionally substituted aminocarbonylalkyl, cyanoalkyl or cycloalkyl, or which is optionally benzo-fused, the benzo radical optionally being substituted by halogen, alkyl, halogenoalkyl, alkoxy, halogenoalkoxy, alkylthio, halogenoalkylthio, amino, alkylamino, dialkylamino, nitro, cyano, alkoxycarbonyl or optionally halogen-substituted alkylenedioxy, and in which, furthermore, R¹ represents a straight-chain or branched alkyl radical.

According to the present invention there is further provided a process for the production of a compound of the present invention characterized in that an N-(2,2,2-trifluoroethyl)-N-alkyl-hydroxy-acetic acid amide of the general formula

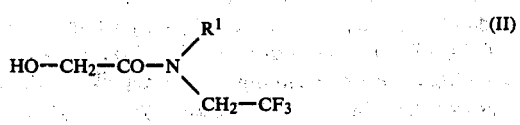
(II)

in which R¹ has the abovementioned meaning, or a salt thereof formed with an acid-binding agent, is reacted with a halogenohetero-arene of the general formula

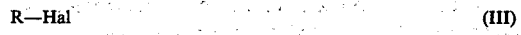

R—Hal (III)

in which
R has the abovementioned meaning and
Hal represents a chlorine or bromine atom, if appropriate in the presence of an acid acceptor and if appropriate in the presence of a diluent.

The new N-(2,2,2-trifluoroethyl)-N-alkyl-azolyloxyacetic acid amides of the formula (I) are distinguished by a powerful herbicidal activity. Surprisingly, the compounds of the formula (I) according to the invention exhibit a considerably more powerful herbicidal action than compounds which are known from the state of the art and have an analogous structure and the same type of action. In addition to a very good action against monocotyledon weeds, they also exhibit a good action against dicotyledon weeds. Because of their good selectivity in respect of cotton, beet, soy beans, wheat and rice, they can be particularly advantageously employed in these crops.

Preferred N-(2,2,2-trifluoroethyl)-N-alkyl-azolyloxyacetic acid amides of formula (I) according to the present invention are those in which R represents the radical

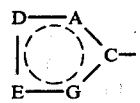

wherein
A represents C—R² or N,
D represents C—R³ or N,
E represents C—R⁴, N, O or S and
G represents C—R⁵, N, O or S,
with the proviso that at least one of the ring members A, D, E or G represents N and at least one of the ring members E or G represents O or S,
and wherein the radicals R², R³, R⁴ and R⁵, which can be identical or different, individually represent a hydrogen or halogen atom, a nitro, cyano, amino, $C_1$–$C_4$-alkylamino, di-$C_1$–$C_4$-alkyl-carbonylamino, $C_1$–$C_4$-alkyl-carbonyl, carboxyl, $C_1$–$C_4$-alkoxy-carbonyl, carbamoyl, $C_1$–$C_4$-alkylamino-carbonyl or di-$C_1$–$C_4$-alkylamino-carbonyl radical, a phenyl-aminocarbonyl radical which is optionally substituted by halogen, nitro or $C_1$–$C_4$-alkyl, a phenyl radical which is optionally substituted by halogen, nitro, cyano, $C_1$–$C_4$-alkyl or $C_1$–$C_4$-alkoxy, an optionally halogen-substituted radical selected from benzyl, phenethyl, $C_1$–$C_4$-alkoxy, $C_2$–$C_4$-alkenoxy, $C_2$–$C_4$-alkinoxy, $C_1$–$C_4$-alkoxy-carbonylmethoxy, benzyloxy, phenoxy, $C_1$–$C_4$-alkylthio, $C_2$–$C_4$-alkenylthio, $C_2$–$C_4$-alkinylthio, $C_1$–$C_4$-alkoxy-carbonylmethylthio, benzylthio, phenylthio, $C_1$–$C_4$-alkyl-sulphinyl, $C_1$–$C_4$-alkylsulphonyl, $C_1$–$C_6$-alkyl, $C_2$–$C_6$-alkenyl and $C_2$–$C_6$-alkinyl, or a cyano-$C_1$–$C_4$-alkyl or $C_1$–$C_4$-alkoxy-$C_1$–$C_2$-alkyl radical, a phenoxy- or phenylthiomethyl radical, a benzyloxy- or benzylthio-methyl radical, a $C_1$–$C_4$-alkylthio-$C_1$–$C_2$-alkyl radical or a $C_1$–$C_4$-alkyl- or phenylsulphinyl-$C_1$–$C_2$-alkyl radical a $C_1$–$C_4$-alkyl- or phenylsulphonyl-$C_1$–$C_2$-alkyl radical, a carboxy-$C_1$–$C_2$-alkyl, $C_1$–$C_4$-alkoxycarbonyl-$C_1$–$C_2$-alkyl, $C_1$–$C_4$-alkylamino-carbonyl-$C_1$–$C_2$-alkyl, di-$C_1$–$C_4$-alkylamino-carbonyl-$C_1$–$C_2$-alkyl, phenylaminocarbonyl-$C_1$–$C_2$-alkyl or $C_3$–$C_{12}$-cycloalkyl radical, or wherein the radicals $R^3$ and $R^4$, together with the adjacent C atoms, represent a fused-on benzo radical, which is optionally substituted by halogen, nitro, cyano or an optionally halogen-substituted radical selected from $C_1$–$C_4$-alkyl, $C_1$–$C_4$-alkoxy, $C_1$–$C_4$-alkylthio and $C_1$–$C_2$-alkylenedioxy; and furthermore $R^1$ represents a $C_1$–$C_6$-alkyl radical.

The invention particularly relates to the compounds of the formula (I) in which R represents one of the following azolyl radicals

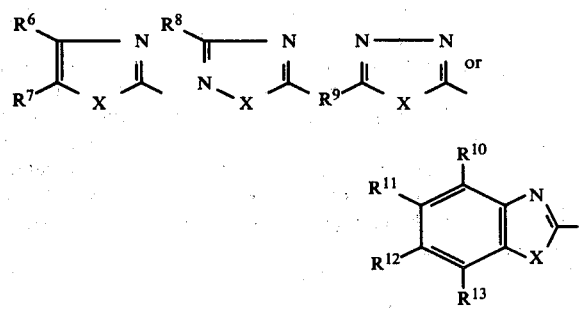

wherein X in each case represents oxygen or sulphur, the radicals $R^6$, $R^7$, $R^8$ and $R^9$, which can be identical or different, individually represent a hydrogen, bromine or chlorine atom, a nitro, cyano, $C_1$–$C_3$-alkyl-carbonyl or $C_1$–$C_3$-alkoxycarbonyl radical, a phenyl radical which is optionally monosubstituted or disubstituted by fluorine, chlorine or bromine, methyl, methoxy, nitro, amino and/or cyano, or a phenoxy, phenylthio, $C_1$–$C_3$-alkylthio, $C_1$–$C_3$-alkoxy, $C_1$–$C_3$-alkylsulphinyl, $C_1$–$C_3$-alkylsulphonyl, $C_1$–$C_4$-alkyl, trifluoromethyl, cyano-$C_1$–$C_4$-alkyl, $C_2$–$C_4$-alkenyl, benzyloxymethyl, $C_1$–$C_3$-alkylamino, N-$C_1$–$C_3$-alkyl-N-$C_1$–$C_4$-alkyl-carbonylamino, phenoxymethylbenzylthio or $C_1$–$C_3$-alkylcarbonyloxy radical and the radicals $R^{10}$, $R^{11}$, $R^{12}$ and $R^{13}$, which can be identical or different, individually represent a hydrogen or chlorine atom or a $C_1$–$C_2$-alkyl, $C_1$–$C_2$-alkoxy, trifluoromethyl or trifluoromethoxy radical, or in each case two of these adjacent radicals together represent methylenedioxy, dichloromethylenedioxy or difluoromethylenedioxy; and in which furthermore, $R^1$ represents a $C_1$–$C_3$-alkyl radical.

If, for example, N-(2,2,2-trifluoroethyl)-N-propylhydroxyacetic acid amide and 2,4,5-trichlorothiazole are used as starting substances, the course of the reaction in the process according to the invention is illustrated by the following equation:

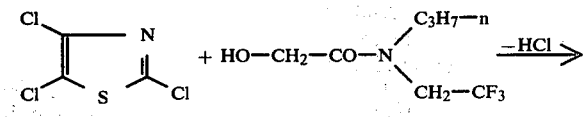

-continued

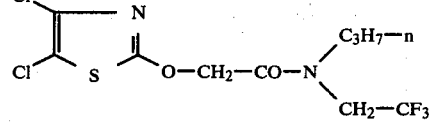

The process for the preparation of the new N-(2,2,2-trifluoroethyl)-N-alkylazolylozyacetic acid amides is preferably carried out using suitable diluents. Possible diluents are water and virtually any of the customary organic solvents. These include, in particular, alcohols (such as methanol, ethanol, n- and iso-propanol and n-, iso-, sec.- and tert.- butanol), ethers (such as diethyl ether, dibutyl ether, tetrahydrofuran and dioxane), ketones (such as acetone, methyl ethyl ketone, methyl isopropyl ketone and methyl isobutyl ketone), nitriles (such as acetonitrile and propionitrile), and the highly polar solvents dimethylformamide, dimethylsulphoxide, sulpholane and hexamethylphosphoric acid triamide.

Virtually any of the acid-binding agents which can customarily be used may be employed as the acid acceptors: these compounds include, in particular, alkali metal hydroxides and oxides and alkaline earth metal hydroxides and oxides (such as sodium hydroxide and potassium hydroxide and calcium oxide or calcium hydroxide), alkali metal carbonates and alkaline earth metal carbonates (such as sodium carbonate, potassium carbonate and calcium carbonate), alkali metal alcoholates (such as sodium methylate, ethylate and tert.-butylate and potassium methylate, ethylate and tert.-butylate), and also aliphatic, aromatic or heterocyclic amines (such as triethylamine, dimethylaniline, dimethylbenzylamine, pyridine, diazabicyclooctane and diazabicycloundecene).

The reaction temperature can be varied within a substantial range. In general, the reaction is carried out at a temperature between $-50°$ and $+150°$ C., preferably at a temperature between $-20°$ and $+100°$ C.

The process according to the invention is in general carried out under normal pressure.

The starting substances of the formulae (II) and (III) are in general employed in approximately equimolar amounts for carrying out the process according to the invention. The components are usually brought together with slight external cooling, and the reaction mixture is stirred until the reaction has ended. The products are isolated by customary methods: if appropriate, some of the diluent is distilled off, and the residue is diluted with water. If the products are thereby obtained as crystals, they are isolated by filtration. Otherwise, the organic products are extracted with a water-immiscible solvent (such as toluene or methylene chloride); after the organic phase has been washed and dried, the solvent is distilled off in vacuo. The products which remain are characterized by their melting points or their refractive indices.

Preferred N-(2,2,2-trifluoromethyl)-N-alkylhydroxyacetic acid amides of formula (II) to be used as starting substances are those in which $R^1$ represents a $C_1$–$C_6$-alkyl radical, and especially a $C_1$–$C_3$-alkyl radical.

Examples of starting substances of the formula (II) which may be mentioned are: N-(2,2,2-trifluoroethyl)-N-methyl-, N-(2,2,2-trifluoroethyl)-N-ethyl-, N-(2,2,2-trifluoroethyl)-N-n-propyl- and N-(2,2,2-trifluoroethyl)-N-iso-propyl-hydroxyacetic acid amide.

The N-(2,2,2-trifluoroethyl)-N-alkyl-hydroxyacetic acid amides of the formula (II) have not yet been described in the literature and form a further subject of the present invention.

The compounds of the formula (II) are obtained when a corresponding acetoxyacetic acid amide of the general formula

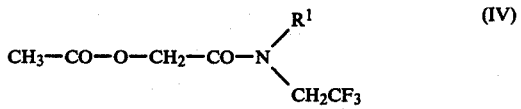

in which $R^1$ has the abovementioned meaning, is reacted with an aqueous-alcoholic alkali metal hydroxide solution (such as with sodium hydroxide in water/methanol (1:1)) at a temperature between 20° and 80° C.

For working up and isolation of the products, the mixture is neutralized with acetic acid and concentrated and the product is extracted from the residue with methylene chloride. After the extraction solution has been dried and filtered, the solvent is carefully distilled off under reduced pressure. The products of the formula (II) remain as an oily or crystalline residue.

Preferred N-(2,2,2-trifluoroethyl)-N-alkylactoxyacetic acid amides of formula (IV) to be used as intermediate products in the production of compounds of formula (II) are those in which $R^1$ represents a $C_1$–$C_6$-alkyl radical, especially a $C_1$–$C_3$-alkyl radical.

Examples of compounds of the formula (IV) which may be mentioned are: N-(2,2,2-trifluoroethyl)-N-methyl-, N-(2,2,2-trifluoroethyl)-N-ethyl-, N-(2,2,2-trifluoroethyl)-N-n-propyl- and N-(2,2,2-trifluoroethyl)-N-isopropyl-acetoxyacetic acid amide.

The compounds of the formula (IV) have not yet been described in the literature and form a further subject of the present invention.

The compounds of formula (IV) are obtained when a corresponding amine of the general formula

in which $R^1$ has the abovementioned meaning, is reacted with an acetoxyacetyl chloride of the general formula

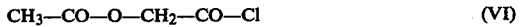

if appropriate in the presence of an acid-binding agent (such as triethylamine) and if appropriate in the presence of a diluent (such as toluene), at a temperature between 10° and 50° C.

For working up, the mixture is filtered, the solvent is distilled off from the filtrate under reduced pressure and the product of the formula (IV) which remains in the residue is purified, if appropriate, by distillation.

Acetoxyacetyl chloride of formula (VI) is already known (see European Published Patent application No. 5,501).

Amines of the formula (V) are also known from the literature and described in previous patent applications (see J. Org. Chem. 24 (1959), 1256–1259; and U.S. patent application Ser. No. 254,718, filed Apr. 16, 1981, now pending; and German Patent application No. P 3,018,030 (Le A 20 329)).

Examples of the amines of the formula (V) which may be mentioned are N-(2,2,2-trifluoroethyl)-N-methylamine, N-(2,2,2-trifluoroethyl)-N-ethylamine and N-(2,2,2-trifluoroethyl)-N-n-propylamine, Preferred halogenohetero-arenes of formula (III) also to be used as starting substances in the production of compounds of formula (I) according to the present invention are those in which R represents those radicals which have already been mentioned in the context of the definitions of the preferred and particularly preferred compounds of formula (I), and Hal represents a chlorine or bromine atom.

Examples of starting substances of the formula (III) which may be mentioned are: 2-chloro- and 2-bromo-oxazole and -thiazole, 2,4-dichloro-, 2,5-dichloro- and 2,4,5-trichloro-oxazole and -thiazole, 4-methyl-, 5-methyl-, 4-tert.-butyl-, 4,5-dimethyl-, 4-methyl-5-cyano, 4-methyl-5-chloro-, 5-methyl-4-chloro-, 4-methyl-5-methoxycarbonyl-, 4-methyl-5-ethoxycarbonyl-, 4-methyl-5-isopropoxycarbonyl-, 4-methyl-5-acetyl-, 5-phenyl-, 4,5-diphenyl-, 4-chloro-5-phenyl-, 4-chloro-5-(3,4-dichlorophenyl)- and 4-methyl-5-phenylthio-2-chloro-oxazole, -2-bromo-oxazole, -2-chloro-thiazole and -2-bromo-thiazole; 3-tert.-butyl-4-cyano-, 3-but-3-en-1-yl -3,4-bis-ethoxycarbonyl-, 3-phenyl- and 3-ethyl-4-phenyl-5-chloro-isoxazole, -5-chloro-isothiazole, -5-bromo-isoxazole and -5-bromo-isothiazole; 3,5-bis-ethoxycarbonyl-4-chloro- and 3,5-bis-ethoxycarbonyl-4-bromo-isoxazole and -isothiazole; 3,5-dichloro-1,2,4-oxadiazole and 3-methyl-, 3-ethyl-, 3-n-propyl-,3-isopropyl-, 3-tert.-butyl-, 3-trifluoromethyl-, 3-trichloromethyl-, 3-methylthio-, 3-methylsulphinyl- and 3-methylsulphonyl-5-chloro-1,2,4-thiadiazole and -5-bromo-1,2,4-thiadiazole; 4-methyl-, 4-ethyl-, 4-n-propyl- and 4-iso-propyl-3-chloro-1,2,5-thiadiazole and -3-bromo-1,2,5-thiadiazole; 2-chloro- and 2-bromo-1,3,4-oxadiazole, 2-chloro- and 2-bromo-1,3,4-thiadiazole and 5-methyl-, 5-ethyl-, 5-n-propyl-, 5-phenyl-, 5-iso-propyl-, 5-tert.-butyl-, 5-bromo-, 5-methylsulphinyl-, 5-ethylsulphinyl-, 5-propylsulphinyl-, 5-methylsulphonyl-, 5-ethylsulphonyl-, 5-propyl-sulphonyl-, 5-methoxycarbonyl-, 5- ethoxy-carbonyl-, 5-(1-cyano2-methylpropyl)-, 5-benzyloxymethyl-, 5-acetylamino-, 5-nitro-, 5-propylthio-, 5-trifluoromethyl-, 5-methylamino- and 5-(N-methyl-N-tert.-butylcarbonyl-amino)2-chloro-1,3,4-oxadiazole, -2-bromo-1,3,4-oxadiazole, -2-chloro-1,3,4-thiadiazole and -2-bromo-1,3,4-thiadiazole; 2-chloro- and 2-bromo-benzoxazole, 2-chloro- and 2-bromo-benzothiazole, 5-methyl-2-chloro-benzoxazole, 2-chloro-6-ethoxy-benzothiazole, 2,5-dichloro-benzoxazole, 2,6-dichlorobenzoxazole, 2-chloro-6-trifluoromethyl-benzothiazole, 2-chloro-5-trifluoromethyloxy-benzothiazole, 2-chloro-5,6-difluoromethylenedioxybenzothiazole, 2,4,6,7-tetrachlorobenzothiazole, 2-chloro-4,6-difluoro-benzothiazole, 2-chloro-5-nitro-benzothiazole, 2-chloro-6-nitro-benzothiazole, 2-chloro-5-nitrobenzoxazole and 2-chloro-5-cyano-benzoxazole.

Halogenoazoles of the formula (III) are known (see Elderfield, Heterocyclic Compounds Volume 5 (1957), page 298 and page 452; Volume 7 (1961), page 463 and page 541; Weissberger, The Chemistry of Heterocyclic Compounds, (a) "Five-Membered Heterocyclic Compounds with Nitrogen and Sulfur or Nitrogen, Sulfur and Oxygen" (1952), page 35 and page 81, (b) "Five and Six-Membered Compounds with Nitrogen and Oxygen" (1962), page 5, page 245 and page 263; Advances in Heterocyclic Chemistry, Volume 5 (1965) page 119; Volume 7 (1966), page 183; Volume 17 (1974), page 99 and Volume 20 (1976), page 65; Synthesis 1978, 803; Tetrahedron Letters 1968, 829; Chem. Ber. 89 (1956), 1534; 90 (1957), 182; 92 (1959), 1928; J. Org. Chem. 27 (1962), 2589; and DE-OS (German Published Specifications) 1,670,706, 1,164,413 and 2,213,865).

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in now way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In addition to a very good action against monocotyledon weeds, the active compounds according to the invention also exhibit a good herbicidal action against dicotyledon weeds. The active compounds according to the invention can be used selectively in various crops, above all in cotton, beet, soy beans and wheat, and also in rice.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They are preferably applied before emergence of the plants, that is to say by the pre-emergence method. They can also be incorporated into the soil before sowing.

the amount of active compound used can vary within a substantial range. It depends essentially on the nature of the desired effect. In general, the amounts used are between 0.05 and 10 kg of active compound per ha, preferably between 0.1 and 8 kg/ha.

The present invention also provides herbicidal compositions containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weed, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

Some of the active compounds according to the invention also exhibit a growth-regulating action when used in certain concentrations.

The examples which follow serve to illustrate the invention more detail.

Preparative Examples
Preparation of compounds of the formula (I)

Example 1

(a) (i)

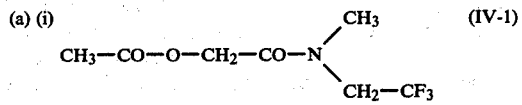

10 g (0.1 mol) of triethylamine and 13.6 g (0.1 mol) of acetoxyacetyl chloride were added to a solution of 9.9 g (0.1 mol) of N-(2,2,2-trifluoroethyl)-N-methylamine in 150 ml of toluene and the mixture was stirred at 20° C. for 15 hours. It was then filtered and the filtrate was distilled. 17 g (79.8% of theory) of N-(2,2,2-trifluoroethyl)-N-methyl-acetoxyacetamide of boiling point 110° C./3 mbar were obtained.

(ii) N—(2,2,2-Trifluoroethyl)-N—ethyl-acetoxyacetamide

-continued

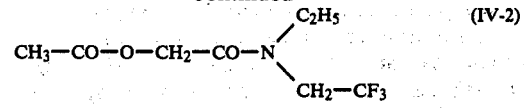

was obtained analogously; $N_D^{20}$:1.4333.

(b) (i)

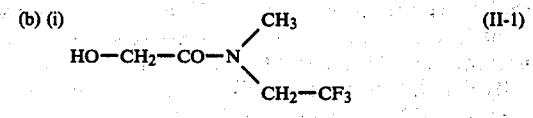

A solution of 15 g (0.07 mol) of N-(2,2,2-trifluoroethyl)-N-methyl-acetoxyacetamide in 100 ml of methanol was added to a solution of 3.1 g of sodium hydroxide in 100 ml of water. The mixture was stirred at 40° C. for 8 hours and then neutralized with acetic acid and concentrated. The concentrate was extracted three times with methylene chloride and the extract was dried and filtered. After the solvent had been distilled off under reduced pressure, 5.7 g (47.5% of theory) of N-(2,2,2-trifluoroethyl)-N-methyl-hydroxy-acetic acid amide remained as an oil, which gradually crystallized: melting point: 38° C.

(ii)

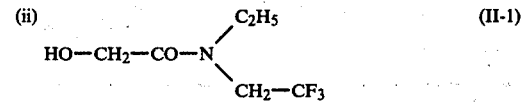

8 ml of saturated sodium hydroxide solution were added to a solution of 20 g (0.088 mol) of N-(2,2,2-trifluoroethyl)-N-ethyl-acetoxyacetamide in 100 ml of methanol. The mixture was stirred at 20° C. for 15 hours and concentrated and the concentrate was neutralized with acetic acid and extracted with methylene chloride. The organic phase was dried and filtered. After the solvent had been distilled off, N-(2,2,2-trifluoroethyl)-N-ethylhydroxyacetic acid amide was obtained as a yellow oil.

(c)

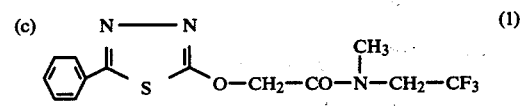

12 g (0.07 mol) of N-(2,2,2-trifluoroethyl)-N-methyl-hydroxyacetic acid amide and 4.5 g of potassium hydroxide powder were dispersed in 100 ml of acetonitrile at 0° C., and a solution of 12 g of 2-chloro-5-phenyl-1,3,4-thiadiazole in 50 ml of acetonitrile was added at 10° C. The mixture was stirred at 30° to 40° C. for 15 hours and concentrated, the concentrate was diluted with water and the mixture was filtered. The crystalline product was recrystallized from isopropanol. 12 g (63% of theory) of N-(2,2,2-trifluoroethyl)-N-methyl-5-phenyl-1,3,4-thiadiazol-2-yl-oxyacetic acid amide of melting point 123° C. were obtained.

Example 2

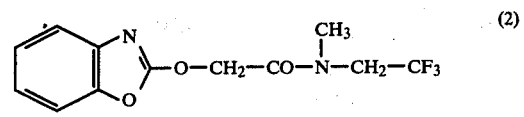

17.1 g (0.1 mol) of N-(2,2,2-trifluoroethyl)-N-methyl-hydroxyacetic acid amide and 7 g of potassium hydroxide powder were initially introduced into 100 ml of acetonitrile at 20° C., and 15.3 g (0.1 mol) of 2-chlorobenzoxazole were added at a temperature between 20° and 40° C. The reaction mixture was stirred at 40° C. for one hour and at 20° C. for a further 15 hours and was concentrated and the concentrate was shaken with toluene and water. The organic phase was washed with dilute sodium hydroxide solution, washed until neutral, dried and filtered. The solvent was carefully distilled off from the filtrate under reduced pressure. 15 g (52% of theory) of N-(2,2,2-trifluoroethyl)-N-methyl-benzoxazol-2-yl-oxy-acetic acid amide of melting point 92° C. were obtained as the residue.

The compounds of formula (I) listed in the table below could be prepared analogously to Example 1 or 2:

$$R-O-CH_2-CO-N\begin{matrix}R^1\\ \\CH_2CF_3\end{matrix} \quad (I)$$

TABLE

Compounds of the formula (I)

| Compound No. | R | $R^1$ | Melting point (°C.) or refractive index ($n_D^{20}$) |
|---|---|---|---|
| (3) | 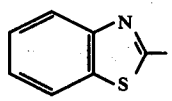 | $CH_3$ | 91 |
| (4) | 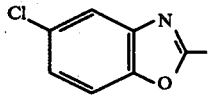 | $CH_3$ | 126 |
| (5) | 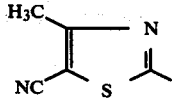 | $CH_3$ | 103 |
| (6) | 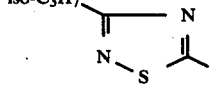 | $CH_3$ | 53 |
| (7) | 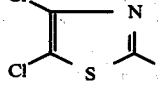 | $CH_3$ | $n_D^{21}$: 1.5088 |
| (8) | 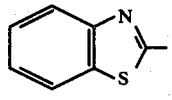 | $C_2H_5$ | 58 |
| (9) | 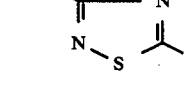 | $CH_3$ | 48 |
| (10) | 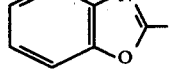 | $C_2H_5$ | 62 |

TABLE-continued

Compounds of the formula (I)

| Compound No. | R | $R^1$ | Melting point (°C.) or refractive index ($n_D^{20}$) |
|---|---|---|---|
| (11) | 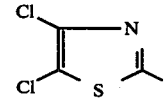 | $C_2H_5$ | |
| (12) | 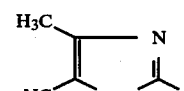 | $C_2H_5$ | 55 |
| (13) | 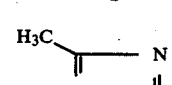 | $CH_3$ | 1.4683 |

The herbicidal activity of the compounds of this invention is illustrated by the following example wherein the compounds according to the present invention are each identified by the number (given in brackets) from Example 2 of the Table hereinabove:

EXAMPLE 3

Pre-emergence test

Solvent: 5 parts by weight of acetone
Emulsifier: 1 part by weight of alkylaryl polyglycol ether To produce a suitable preparation of active compound 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

In this test, for example, the following compounds showed an excellent activity: (2), (4), (5), (6) and (7).

It will be understood that the specification and examples are illustrative but not limitative of the present invention and that other embodiments within the spirit and scope of the invention will suggest themselves to those skilled in the art.

We claim:

1. An N-(2,2,2-trifluoroethyl)-N-alkyl-azolylacetic acid amide of the formula

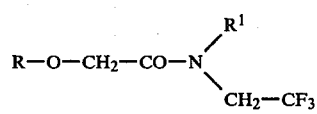

in which
R represents

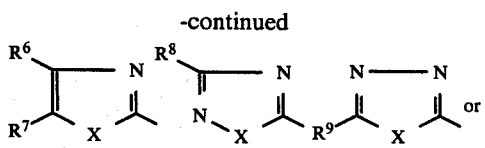 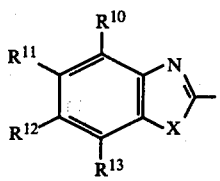

X in each case represents oxygen or sulphur, the radicals $R^6$, $R^7$, $R^8$ and $R^9$, which can be identical or different, individually represent a hydrogen, bromine or chlorine atom, a nitro, cyano, $C_1$–$C_3$-alkyl-carbonyl or $C_1$–$C_3$-alkoxycarbonyl radical, a phenyl radical which is optionally monosubstituted or disubstituted by fluorine, chlorine or bromine, methyl, methoxy, nitro, amino and/or cyano, or a phenoxy, phenylthio, $C_1$–$C_3$-alkylthio, $C_1$–$C_3$-alkoxy, $C_1$–$C_3$-alkylsulphinyl, $C_1$–$C_3$-alkylsulphonyl, $C_1$–$C_4$-alkyl, trifluoromethyl, cyano-$C_1$–$C_4$-alkyl, $C_2$–$C_4$-alkenyl, benzyloxymethyl, $C_1$–$C_3$-alkylamino, $N$-$C_1$–$C_3$-alkyl-$N$-$C_1$–$C_4$-alkyl-carbonylamino, phenoxymethylbenzylthio or $C_1$–$C_3$-alkyl-carbonyloxy radical and the radicals $R^{10}$, $R^{11}$, $R^{12}$, and $R^{13}$, which can be identical or different, individually represent a hydrogen or chlorine atom or a $C_1$–$C_2$-alkyl, $C_1$–$C_2$-alkoxy, trifluoromethyl or trifluoromethoxy radical, or in each case two of these adjacent radicals together represent methylenedioxy, dichloromethylenedioxy or difluoromethylenedioxy; and $R^1$ represents a $C_1$–$C_6$-alkyl radical.

2. A compound according to claim 1, in which $R^1$ is a $C_1$–$C_3$-alkyl radical.

3. A compound according to claim 1, wherein said compound is N-(2,2,2-trifluoroethyl)-N-methyl-benzoxazol-2-yl-oxy-acetic acid amide of the formula

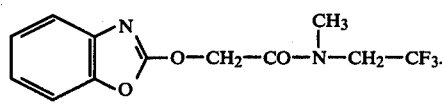

4. A compound according to claim 1, wherein said compound is N-(2,2,2-trifluoroethyl)-N-methyl(5-chlorobenzoxazol-2-yl-oxy)-acetic acid amide of the formula

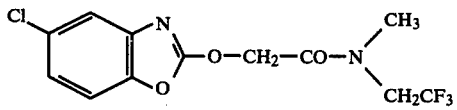

5. A compound according to claim 1, wherein said compound is N-(2,2,2-trifluoroethyl)-N-methyl-(5-cyano-4-methyl-1,3-thiazol-2-yl-oxy)-acetic acid amide of the formula

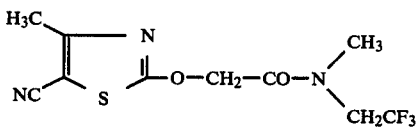

6. A compound according to claim 1, wherein said compound is N-(2,2,2-trifluoroethyl)-N-methyl-(3-isopropyl-1,2,4-thiadiazol-5-yl-oxy)-acetic acid amide of the formula

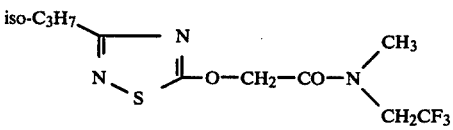

7. A compound according to claim 1, wherein said compound is N-(2,2,2-trifluoroethyl)-N-methyl-(4,5-dichloro-1,3-thiazol-2-yl-oxy)-acetic acid amide of the formula

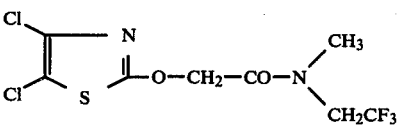

8. A herbicidal composition comprising a herbicidally effective amount of a compound according to claim 1 in admixture with a diluent.

9. A method of combating weeks comprising applying to the weeds, or to a habitat thereof, a herbicidally effective amount of a compound according to claim 1.

10. The method according to claim 9, wherein said compound is
N-(2,2,2-trifluoroethyl)-N-methyl-benzoxazol-2-yl-oxy-acetic acid amide,
N-(2,2,2-trifluoroethyl)-N-methyl-(5-chlorobenzoxazol-2-yl-oxy)-acetic acid amide,
N-(2,2,2-trifluoroethyl)-N-methyl-(5-cyano-4-methyl-1,3-thiazol-2-yl-oxy)-acetic acid amide.
N-(2,2,2-trifluoroethyl)-4-methyl-(3-isopropyl-1,2,4-thiadiazol-5-yl-oxy)-acetic acid amide or
N-(2,2,2-trifluoroethyl)-N-methyl-(4,5-dichloro-1,3-thiazol-2-yl-oxy)-acetic acid amide.

* * * * *